United States Patent [19]

Chen et al.

[11] Patent Number: 4,766,209
[45] Date of Patent: Aug. 23, 1988

[54] AMINO SUGAR CARBONATING AGENTS AND THEIR PREPARATION

[75] Inventors: Teh-Kuei Chen, Gaylordsville, Conn.; Dorothy J. Muffett, Bloomington, Minn.; Karen G. Tandy, Litchfield, Conn.

[73] Assignee: Nestec S. A., Vevey, Switzerland

[21] Appl. No.: 837,718

[22] Filed: Mar. 10, 1986

[51] Int. Cl.$^4$ .................. C07H 5/04; C07H 5/06; C07H 3/00; C08B 37/00
[52] U.S. Cl. .................. 536/55.3; 536/55.2; 536/124
[58] Field of Search .............. 536/55.2, 55.3, 124

[56] References Cited

U.S. PATENT DOCUMENTS

| | | | |
|---|---|---|---|
| 2,297,734 | 10/1942 | Wyler et al. | 536/55.3 |
| 3,518,343 | 6/1970 | Welsh et al. | 424/148 |
| 4,127,645 | 11/1978 | Witzel et al. | 424/154 |
| 4,371,616 | 2/1983 | Huibers | 536/124 |
| 4,579,742 | 4/1986 | Lavie | 426/96 |

FOREIGN PATENT DOCUMENTS

| | | | |
|---|---|---|---|
| 0191464 | 8/1986 | European Pat. Off. | 536/124 |
| 1295343 | 3/1959 | France | 536/55.2 |
| 1225280 | 10/1986 | Japan | 536/124 |
| 2179038A | 2/1987 | United Kingdom | 536/46 |

OTHER PUBLICATIONS

Chemical Abstracts; Lavie, L., vol. 98, (1983), 87942d.

Primary Examiner—Ronald W. Griffin
Assistant Examiner—Nancy S. Carson
Attorney, Agent, or Firm—Vogt & O'Donnell

[57] ABSTRACT

Carbonating agents are prepared by reacting bicarbonate ions with the amino moiety of glucosamine or galatosamine in aqueous solution to form glucoasamine bicarbonate or galactosamine bicarbonate. The bicarbonate is then isolated by drying. The resulting dry 2-amino sugar bicarbonate is stable at room temperature and can be used as a carbonating agent. It may be used with other constituents to form a dry beverage mix. Upon rehydration, the 2-amino sugar bicarbonate releases carbon dioxide and additionally imparts a mild sweet taste to the carbonated beverage.

11 Claims, No Drawings

AMINO SUGAR CARBONATING AGENTS AND THEIR PREPARATION

This invention pertains to dry carbonating agents, methods of preparing and using such agents and the products incorporating such agents. A dry carbonating agent is a substance which releases carbon dioxide upon contact with water. Such agents may be used in food, beverage and pharmaceutical applications in which effervescence is desired. A dry carbonating agent can be mixed with other materials such as diluents, carriers and flavorings and can thereafter be reconstituted as a carbonated beverage.

Dry carbonating agents having good effervescent qualities without adverse taste effects have long been sought in the prior art. Primarily, the existing dry carbonating agents have included the metallic salts of inorganic carbonates or bicarbonates, the most common of which is sodium bicarbonate. However, these inorganic carbonating agents generally have imparted off-flavors and saline tastes to the product because of the metallic ions released upon reaction of the carbonating agent with water.

Certain oxygen, nitrogen and sulfur carboxyanhydride compositions are described in U.S. Pat. Nos. 3,441,417 and 3,649,298 as organic carbon dioxide carriers in dry carbonating agent applications. However, the processes described to make these organic carbonating agents require phosgene gas which, because of possible toxicological problems, is undesirable in food applications.

A process for the preparation of a L-lysine carbamate as an organic carbon dioxide carrier for effervescent compositions was described in UK Patent Application No. GB 2,037,760 A.

SUMMARY OF THE INVENTION

The present invention substantially avoids the disadvantages discussed above. The present invention includes the discovery that bicarbonates of the 2-amino sugars, glucosamine and galactosamine, may be used as dry carbonating agents. The 2-amino sugar bicarbonates readily release carbon dioxide upon contact with water and provide a mild sweet taste to the resulting carbonated aqueous liquid. Accordingly, such dry carbonating agents are particularly well-suited for use in beverage mixes.

The present invention also provides a method for preparing a dry, stable carbonating agent which comprises reacting the amino moiety of glucosamine or galactosamine in aqueous solution with bicarbonate ions so as to form a solution of glucosamine or galactosamine bicarbonate, and then isolating the bicarbonate from the solution by drying.

In one embodiment of the present invention, the bicarbonate ions are reacted with the amino group by preparing an aqueous solution of the free 2-amino sugar and then introducing carbon dioxide into the solution. In another embodiment of the present invention, the reaction of the bicarbonate ions with the amino moiety is effected by contacting a salt of the 2-amino sugar with a strongly basic ion exchange resin which has been charged with bicarbonate ions. The anion of the salt is removed from the 2-amino sugar and replaced by the bicarbonate ion, thereby forming the 2-amino sugar bicarbonate.

DETAILED DESCRIPTION OF THE EMBODIMENTS

The process of the present invention utilizes the naturally occurring 2-amino sugars 2-amino-2-deoxy-D-glucose (glucosamine) or 2-amino-2-deoxy-D-galactose (galactosamine). These 2-amino sugars are usually obtained from natural polysaccharide sources such as chitin (glucosamine), and collagenous material such as tendon and cartilage (galactosamine). Such 2-amino sugars are typically recovered in the form of their mineral acid salts such as the hydrochloride.

Thus, glucosamine hydrochloride can be obtained by the well-known procedure of the mineral acid hydrolysis of chitin, which is a polysaccharide wherein the primary repeating unit is N-acetylglucosamine. Chitin is readily prepared by well-known means from shells of Crustacea such as crab, shrimp, lobster, crayfish and the like.

An aqueous solution of the free amino sugar may then be prepare by neutralizing the acidic hydrochloride solution, preferably by passing it through an ion exchange column. Any suitable weakly basic anion exchange resin can be used in the present invention to prepare the free amino sugar solution, such as, for example, DOWEX MWA-1 (The Dow Chemical Company). The column is charged to hydroxide form with a suitable hydroxide solution such as a 5% aqueous solution of sodium hydroxide. This charges the active sites of the ion exchange resin with hydroxide to prepare for the ion exchange reaction.

The aqueous solution of the amino sugar salt is then passed through the prepared column at a rate sufficient to allow the ion exchange reaction to occur. The column is then eluted through with deionized water. The fractions of eluate which have an alkaline pH will contain 2-amino sugar free base. It is preferred to collect the fractions which have a pH greater than 8. Later eluate fractions which have a lower pH exhibit less complete conversion to the free base. This results in the presence of the acid salt in sufficient concentration so as to detract from the flavor quality of the final bicarbonate product.

Glucosamine and galactosamine hydrochlorides are readily soluble in water and aqueous solutions can be easily prepared by dissolving the hydrochloride in water. Concentrations for the glucosamine hydrochloride, for example, may be up to 25% by weight, depending on the viscosity desired. If the aqueous hydrochloride solution is to be passed through an ion exchange resin to prepare the free base, then lower concentrations may be prepared in order to prevent problems attendant with high viscosity of solutions passed through ion exchange columns. In basic ion exchange procedures using, for example, the glucosamine hydrochloride, the rate of undesired browning reactions of the free amino sugar increases with increasing concentration. It is thus particularly important that for higher concentrations the flow rate through the column, as well as subsequent processing of the 2-amino sugar, be as rapid as practicable. Chilling the column during the ion exchange, preferably to below 15° C., will further aid in minimizing such undesirable degradative reactions.

The aqueous solution of the free amino sugar is then reacted with a suitable source of bicarbonate ions to make the 2-amino sugar bicarbonate of the present invention. In a preferred embodiment of the present invention, this is done by carbonating the amino sugar solution, i.e., by contacting it with carbon dioxide. Such carbonation may be effected with either gaseous $CO_2$ or dry ice. The solubility of carbon dioxide in aqueous solutions and the various carbonate species that are formed influence the reaction with the amino sugar. For simple aqueous carbonate solutions the interdependent nature of the equilibrium concentrations of the four solute components—$CO_2$, $H_2CO_3$, $HCO_3^-$, $CO_3^{2-}$—can be represented by the following equilibrium reactions:

$$CO_2(g) \rightleftharpoons CO_2(aq)$$

$$CO_2(aq) + H_2O \rightleftharpoons H_2CO_3$$

$$H_2CO_3 \rightleftharpoons H^+ + HCO_3^-$$

$$HCO_3^- \rightleftharpoons H^+ + CO_3^{2-}$$

At pH values of 7 to 10 the bicarbonate species—$HCO_3^-$—predominates in aqueous solution. Moreover, as the pKa constants for the amino group of the 2-amino sugars are also about 10 (glucosamine=9.7), as the pH falls below that level, more and more of the amino groups will react with the bicarabonate ions to form the amino sugar bicarbonate. As the carbonation of the collected eluate fractions (pH 8-10) proceeds, the pH of the solution drops and more bicarbonate ion forms and reacts with the amino sugar. At the end of the carbonation step, the solution has reached a pH range of about 6-7.

In order to enhance the solubilization of the carbon dioxide and the reaction with the 2-amino sugar, it is preferred to maintain the solution at temperatures below ambient, preferably below 10° C. A 5-10% increase in carbonation yield may be obtained by maintaining the solutions at 0°-2° C. instead of 25° C. Addition of dry ice will both lower the temperature of the solution and introduce carbon dioxide into the solution. The yield of bicarbonate is also augmented by increasing the pressure during carbonation up to about 690 kPa (100 psi). At 690 kPa, yield improves with increasing duration of the carbonation step up to about 90 minutes. Higher pressures or longer times were not found to be further significantly advantageous.

In an alternative embodiment of the present invention, the aqueous solution containing the desired aminosugar bicarbonate may be formed directly from an amino sugar salt by an ion exchange procedure. In this embodiment, an aqueous solution of a salt of the 2-amino sugar, such as the hydrochloride, is contacted with a strongly basic ion exchange resin charged with bicarbonate ion. This may be done by first eluting a column of the resin with sodium or potassium bicarbonate. The aqueous solution of the amino sugar hydrochloride is then passed through the column. The chloride ion is removed from the salt and replaced by the bicarbonate ion, so that the resulting eluate contains the amino sugar bicarbonate.

The amino sugar bicarbonate in aqueous solution can be isolated by drying the solution such as by freeze drying, spray drying or vacuum drying. The amino sugar bicarbonate in the solution is sensitive to heat which may cause release of $CO_2$ as well as other undesirable degradative reactions. Because of such thermal instability, the drying procedure employed should avoid prolonged exposure to elevated temperatures or excessively high temperatures. The preferred drying technique is to freeze dry the aqueous solution. It is also preferable to maintain the temperature of the carbon dioxide and amino sugar reaction mixture, and the resulting bicarbonate solution, at below 15° C. and to freeze the bicarbonate solution as soon as possible in preparation for freeze drying.

The freeze drying step is continued until the product has a moisture content of less than 8% by weight and preferably less than 5%. The resulting dry amino sugar bicarbonate is a white powder.

The dry amino sugar bicarbonate thus isolated is stable at room temperature and possesses a characteristic mild sweet taste. It can absorb moisture when exposed to air, the freeze dried product being particularly hygroscopic. Accordingly, in packaging the product of the present invention, care should be exercised to avoid product moisture. Thus, dry beverage compositions which include the bicarbonate of the present invention as an ingredient should be stored in sealed, air-tight, moisture-free containers.

The addition of carriers to the solution of 2-amino sugar bicarbonates can serve to reduce the hygroscopicity of the final product as well as aid in the drying step. Good carriers should have the ability to bind water so that it is not free to cause stickiness or encourage $CO_2$ loss or browning. Acidic conditions promote the release of $CO_2$ from the bicarbonate. Consequently, carriers such as maltodextrin and gum arabic, because of their low pH, reduce $CO_2$ retention and are less preferred. Certain modified dextrins, however, have a non-acidic pH and appear to be more suitable for such applications. One such modified dextrin, N-ZORBIT (National Starch & Chemical) was found particularly useful as a carrier.

Upon reconstitution in an aqueous solution, the amino sugar bicarbonate releases carbon dioxide. In general, the release of carbon dioxide may be represented by the following formula $$RNH_2H_2CO_3 + H^+ \rightleftharpoons RNH_3^+ + H_2O + CO_2$$

where R is the 2-amino sugar, without the amino group. Preferably, the pH of the solution is acidic in order to promote release of carbon dioxide.

In addition to releasing carbon dioxide, the carbonating agent of the present invention additionally imparts a mild sweet taste to the solution thus carbonated. Thus, the carbonating agent of the present invention may be especially suitable in beverage applications where a sweet taste is often desirable. In such applications, utilization of the amino sugar bicarbonate as the carbonating agent would make possible a reduction in the amount of sugar that would ordinarily be added. Suitable dry diluents, carriers and flavorings can be admixed with the bicarbonate to form a dry beverage composition. While especially useful as part of a dry beverage composition, the carbonating agent of the present invention may also be used in other applications in which the release of carbon dioxide is desirable upon the addition of water.

The following Examples are set forth to illustrate certain embodiments of the present invention. They are not to be construed, however, as limiting the invention in any manner. Unless otherwise indicated, all percentages are given by weight.

EXAMPLE I

DOWEX MWA-1 macroporous basic ion exchange resin is washed with 6N HCl and then with deionized water. The resin is then packed in a 9.5 cm glass column up to 80 cm in height. The packed column is washed thoroughly with deionized water. Then 12 liters of 5% NaOH solution are passed through the column followed by sufficient deionized water so that the eluate has the same pH as the deionized water. The whole column is then cooled to below 8° C.

1200 ml of an 18% solution of glucosamine hydrochloride in deionized water (15° C.) is passed through the column at a rate of 25 ml/min, followed by cold deionized water (15° C.) at the same rate of elution. The eluate fractions (300–500 ml each) having a pH higher than 8.3 are collected and then carbonated at 276 kPa (40 psi) of $CO_2$ at 10° C. for 1 hr. The resulting solution is then frozen and freeze dried to a final moisture content of 5.0–6.5%. The combined yield is 155 g. The final freeze dried glucosamine bicarbonate has a chloride content of less than 0.6%. The average $CO_2$ yield from the product is 75–88 ml/g (corrected to standard conditions of 0° C. and 760 mm Hg) compared to a theoretical $CO_2$ content for glucosamine bicarbonate of 93 ml/g. Melting point determinations for the 88 ml/g product give a decomposition commencing at 93° C. IR spectra are consistent with the formation of the amino-bicarbonate salt bond.

EXAMPLE II

| Ingredients | Dry Beverage Mix % | Content as consumed % |
| --- | --- | --- |
| Sugar | 61.79 | 9.20 |
| Citric Acid | 4.84 | 0.72 |
| Malic Acid | 4.84 | 0.72 |
| Apple Juice Solids | 3.81 | 0.57 |
| Instant Tea Powder | 0.46 | 0.07 |
| Apple Flavor | 0.38 | 0.06 |
| Peach Flavor | 0.08 | 0.01 |
| Glucosamine bicarbonate | 23.80 | 3.54 |
| Water | — | 85.11 |
| | 100.00 | 100.00 |

Glucosamine bicarbonate produced according to the procedure described in Example I, and having a $CO_2$ content of 75 ml/g is blended with the other dry ingredients noted in the table above, in order to obtain a uniform mixture. 21 g of the resulting dry beverage mix is stirred into 120 ml of cold water. It takes about 30–40 seconds for complete dissolution and the drink continues to evolve $CO_2$ bubbles for 3–4 minutes. The prepared drink evolves 3 volumes of $CO_2$ per volume of liquid.

EXAMPLE III

| Ingredients | Dry Beverage Mix % | Content as consumed % |
| --- | --- | --- |
| Sugar | 78.71 | 10.51 |
| Citric Acid | 6.00 | .80 |
| Monocalcium Phosphate | 0.26 | 0.03 |
| Strawberry Flavor | 0.69 | 0.09 |
| Red #40 (coloring) | 0.07 | 0.01 |
| Glucosamine bicarbonate | 14.27 | 1.91 |
| Water | — | 86.64 |
| | 100.00 | 100.00 |

The formulation containing the above ingredients is prepared using glucosamine bicarbonate obtained in the same manner as in Example I. 18.5 g of the mixture is used to make 120 ml of carbonated soft drink. A complete solution is obtained in about 30–45 seconds and the observable bubbling lasts about 3 minutes. The prepared drink evolves about 2 volumes of $CO_2$ for each volume of liquid.

EXAMPLE IV

DOWEX MSA-2 ion exchange resin (strong base type II, macroporous S-DVB spherical beads) is washed with 6N HCl and rinsed with deionized water. The resin is packed into a 9.5 cm diameter column up to 80 cm in height. The column is then eluted thoroughly with deionized water. 8 liters of a 5% solution of $NaHCO_3$ are passed through the column followed by elution with deionized water until the eluate has the same pH as the deionized water.

700 ml of a 20% solution of glucosamine hydrochloride in deionized water is passed through the column at a rate of 25 ml/minute followed by deionized water elution. The eluate fractions (500–600 ml) having a pH of 6.85–7.40 are collected, frozen and freeze dried to a final moisture content of 5.8–7.2%. The combined yield is 98 g. The freeze dried product has a chloride content of 2.0–2.5%. The average $CO_2$ content of the product is 60 ml/g.

We claim:

1. A method for preparing a carbonating agent which comprises reacting bicarbonate ions with a 2-amino sugar selected from the group consisting of glucosamine and galactosamine in aqueous solution for forming a bicarbonate selected from the group consisting of glucosamine bicarbonate and galactosamine bicarbonate in the solution and then drying the solution for isolating the bicarbonate in a dry stable form.

2. The method of claim 1 wherein the bicarbonate is isolated by drying the solution by freeze drying.

3. The method of claim 1 or 2 wherein the aqueous solution is a solution of a mineral acid salt of the 2-amino sugar and the bicarbonate ions are reacted with the 2-amino sugar by charging a strongly basic ion exchange resin with bicarbonate ions and contacting the charged resin with the aqueous solution.

4. The method of claim 1 or 2 wherein the bicarbonate ions are reacted with the 2-amino sugar by introducing carbon dioxide into the aqueous solution of the 2-amino sugar.

5. The method of claim 4 further comprising first passing an aqueous solution of a hydrochloride of the 2-amino sugar through a weakly basic ion exchange column for obtaining eluate fractions and then collecting the eluate fractions having a pH above 8 for obtaining the aqueous solution of the 2-amino sugar.

6. The method of claim 4 wherein the aqueous solution is maintained in contact with gaseous $CO_2$ at a pressure of from about 276 kPa to about 690 kPa for about 60 minutes to about 90 minutes.

7. The product of the method of claim 1 or 2.

8. The product of the method of claim 3.

9. The product of the method of claim 4.

10. Glucosamine bicarbonate.

11. Galactosamine bicarbonate.

* * * * *

UNITED STATES PATENT AND TRADEMARK OFFICE
CERTIFICATE OF CORRECTION

PATENT NO.   : 4,766,209

DATED        : August 23, 1988

INVENTOR(S)  : Teh-Kuei Chen, et al.

It is certified that error appears in the above-identified patent and that said Letters Patent is hereby corrected as shown below:

On the title page, under the heading "U.S. Patent Documents", "10/1942" should be --12/1940--.

On the title page in line 3 of the abstract, "glucoasamine" should be --glucosamine--.

Column 1, line 37, delete "No.".

Column 2, line 21, "prepare" should be --prepared--.

Column 4, line 36, after "formula" insert--:--.

Signed and Sealed this

Twenty-first Day of March, 1989

Attest:

DONALD J. QUIGG

*Attesting Officer*           *Commissioner of Patents and Trademarks*